US011028157B2

(12) United States Patent
Juraszek et al.

(10) Patent No.: US 11,028,157 B2
(45) Date of Patent: Jun. 8, 2021

(54) BINDING MOLECULES THAT SPECIFICALLY BIND TO TAU

(71) Applicant: JANSSEN VACCINES & PREVISION B.V., Leiden (NL)

(72) Inventors: Jaroslaw Juraszek, Amsterdam (NL); Constantin Adrian Apetri, Noordwijkerhout (NL)

(73) Assignee: JANSSEN VACCINES & PREVENTION B.V., Leiden (NL)

( * ) Notice: Subject to any disclaimer, the term of this patent is extended or adjusted under 35 U.S.C. 154(b) by 104 days.

(21) Appl. No.: 16/497,916

(22) PCT Filed: Mar. 27, 2018

(86) PCT No.: PCT/EP2018/057770
§ 371 (c)(1),
(2) Date: Sep. 26, 2019

(87) PCT Pub. No.: WO2018/178077
PCT Pub. Date: Oct. 4, 2018

(65) Prior Publication Data
US 2021/0122810 A1 Apr. 29, 2021

(30) Foreign Application Priority Data
Mar. 28, 2017 (EP) ..................... 17163425

(51) Int. Cl.
*C07K 16/18* (2006.01)
(52) U.S. Cl.
CPC .......... *C07K 16/18* (2013.01); *C07K 2317/21* (2013.01); *C07K 2317/56* (2013.01); *C07K 2317/565* (2013.01); *C07K 2317/92* (2013.01)
(58) Field of Classification Search
None
See application file for complete search history.

(56) References Cited

U.S. PATENT DOCUMENTS 10,400,034 B2 * 9/2019 Wadia ................... A61K 39/395
10,562,963 B2 * 2/2020 Wadia ................... A61K 39/395

FOREIGN PATENT DOCUMENTS

WO 2013/041962 A1 3/2013
WO 2015/197820 A1 12/2015

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1): 146-52 (Year: 1994).*
Abhinandan, K.R., et al. "Analysis and improvements to Kabat and structurally correct numbering of antibody variable domains", Molecular Immunology, 45, pp. 3832-3839. (2008).
Almagro, J. C. "Identification of differences in the specificity-determining residues of antibodies that recognize antigens of different size: implications for the rational design of antibody repertoires", Journal of Molecular Recognition, 17, pp. 132-143. (2004).
Aluise, C. D., et al. "Peptides and proteins in plasma and cerebrospinal fluid as biomarkers for the prediction, diagnosis, and monitoring of therapeutic efficacy of Alzheimer's disease", Biochimica et Biophysica Acta, 1782, pp. 549-558. (2008).
Arriagada, P. V., et al. "Neurofibrillary tangles but not senile plaques parallel duration and severity of Alzheimer's disease", Neurology, 42, pp. 631-639. (Mar. 1992).
Asuni, A. A., et al. "Immunotherapy Targeting Pathological Tau Conformers in a Tangle Mouse Model Reduces Brain Pathology with Associated Functional Improvements", The Journal of Neuroscience, 27(34), pp. 9115-9129. (Aug. 22, 2007).
Bancher, C. "Neuropathological staging of Alzheimer lesions and intellectual status in Alzheimer's and Parkinson's disease patients", Neuroscience Letters, 162, pp. 179-182. (1993).
Barghorn, S., et al. "Purification of Recombinant Tau Protein and Preparation of Alzheimer-Paired Helical Filaments in Vitro", Methods in Molecular Biology, vol. 299: Amyloid Proteins: Methods and Protocols, pp. 35-51. (2005).
Boimel, M., et al. "Efficacy and safety of immunization with phosphorylated tau against neurofibrillary tangles in mice", Experimental Neurology, 224, pp. 472-485. (2010).
Boutajangout, A., et al. "Immunotherapy Targeting Pathological Tau Prevents Cognitive Decline in a New Tangle Mouse Model", The Journal of Neuroscience, 30(49), 16559-16566. (Dec. 8, 2010).
Boutajangout, A., et al. "Passive immunization targeting pathological phospho-tau protein in a mouse model reduces functional decline and clears tau aggregates from the brain", Journal of Neurochemistry, 118, pp. 658-667. (2011).
Braak, H., et al. "Frequency of Stages of Alzheimer-Related Lesions in Different Age Categories", Neurobiology of Aging, vol. 18, No. 4, pp. 351-357. (1997).
Cairns, N. J., et al. "TDP-43 in Familial and Sporadic Frontotemporal Lobar Degeneration with Ubiquitin Inclusions", The American Journal of Pathology, vol. 171, No. 1, pp. 227-240. (2007).
Anonymous "Anti-Human Tau Therapeutic Antibody (CBTAU-27.1)13 TAB-0211CL", 2 pages. (Oct. 31, 2016).
Chai, X., et al. "Passive Immunization with Anti-Tau Antibodies in Two Transgenic Models: Reduction of Tau Pathology and Delay of Disease Progression", The Journal of Biological Chemistry, vol. 286, No. 39, pp. 34457-34467. (Sep. 30, 2011).
Chothia, C., et al. "Canonical Structures for the Hypervariable Regions of Immunoglobulins", J. Mol. Biol., 196, pp. 901-917. (1987).

(Continued)

*Primary Examiner* — Adam Weidner
(74) *Attorney, Agent, or Firm* — Kramer Amado

(57) ABSTRACT

The invention relates to binding molecules and antigen-binding fragments that specifically bind to microtubule-associated protein tau. The invention also relates to diagnostic, prophylactic and therapeutic methods using the binding molecules or antigen-binding fragments.

20 Claims, 4 Drawing Sheets
Specification includes a Sequence Listing.

(56) References Cited

OTHER PUBLICATIONS

Cragg, M. S. "CD20 antibodies: doing the time warp", Blood 118 (2), pp. 219-220. (Jan. 2, 2017).
Drechsel, D. N., et al. "Modulation of the Dynamic Instability of Tubulin Assembly by the Microtubule-Associated Protein Tau", Molecular Biology of the Cell, vol. 3, pp. 1141-1154. (Oct. 1992).
Frost, B., et al. "Propagation of Tau Misfolding from the Outside to the Inside of a Cell", The Journal of Biological Chemistry, vol. 284, No. 19, pp. 12845-12852. (2009).
Gendron, T. F., et al. "The role of tau in neurodegeneration", Molecular Neurodegenration, 4:13, pp. 1-19. (2009).
Gomez-Isla, T., et al. "Neuronal Loss Correlates with but Exceeds Neurofibrillary Tangles in Alzheimer's Disease", the American Neurological Association, 41, pp. 17-24. (1997).
Hromadkova, L., et al. "Difficulties assoicated with the structural analysis of proteins susceptible to form aggregates: The case of Tau protein as a biomaker of Alzheimer's disease", J. Sep. Sci. 39, pp. 799-807. (2016).
Jeganathan, S., et al. "The Natively Unfolded Character of Tau and Its Aggregation to Alzheimer-like Paired Helical Filaments", Biochemistry, 47, pp. 10526-10539. (2008).
Khlistunova, I., et al. "Inducible Expression of Tau Repeat Domain in Cell Models of Tauopathy Aggregation Is Toxic to Cells But Can Be Reversed by Inhibitor Drugs", The Journal of Biologicial Chemistry, vol. 281, No. 2, pp. 1205-1214. (2006).
Lefranc, M-P., et al. "IMGT unique numbering for immunoglobulin and T cell receptor variable domains and Ig superfamily V-like domains", Developmental and Comparative Immunology, 27, pp. 55-77. (2003).
Mandelkow, E-M., et al. "Biochemistry and Cell Biology of Tau Protein in Neurofibrillary Degeneration", Cold Spring Harbor in Medicine, 2, pp. 1-26. (2012).
Bernova, J. "Investigating novel approaches to linear epitope mapping; biophysical characterization of tau protein and its interactions with anti-tau antibodies", Master's Thesis, Institute of Biophysics, University of Linz, pp. 1-9. (Oct. 30, 2015).
Morris, M., et al. "The Many Faces of Tau", Neuron, 70, pp. 410-426. (2011).
Nicholson, A. M., et al. "Increased Membrane Cholesterol Might Render Mature Hippocampal Neurons More Susceptible to β-Amyloid-Induced Calpain Activation and Tau Toxicity", The Journal of Neuroscience, 29(14), pp. 4640-4651. (2009).
Oakley, H., et al. "Intraneuronal β-Amyloid Aggregates, Neurodegeneration, and Neuron Loss in Transgenic Mice and Five Familial Alzheimer's Disease Mutations: Potential Factors in Amyloid Plaque Formation", The Journal of Neuroscience, 26(40), pp. 10129-10140. (2006).
Petry, F. R., et al. "Specificity of Anti-Tau Antibodies when Analyzing Mice Models of Alzheimer's Disease: Problems and Solutions", PLOS ONE, vol. 9, No. 5, 12 pages. (May 2, 2014).
Polydoro, M., et al. "Age-Dependent Impairment of Cognitive and Synaptic Function in the htau Mouse Model of Tau Pathology", The Journal Neuroscience, 29(24), pp. 10741-10749. (2009).
Raj, A., et al. "A Network Diffusion Model of Disease Progression in Dementia", Neuron, 73, pp. 1204-1215. (2012).
Rapoport, M., et al. "Tau is essential to β-amyloid-induced neurotoxicity", PNAS, 99:9, pp. 6364-6369. (2002).
Roberson, E. D. "Reducing Endogenous Tau Ameliorates Amyloid β-Induced Deficitts in an Alzheimer's Disease Mouse Model", Science, vol. 316, pp. 750-754. (2007).
Rosenmann, H., et al. "Tauopathy-like Abnormalities and Neurologic Deficits in Mice Immunized With Neuronal Tau Protein", Arch Neurol., 63(10), pp. 1459-1467. (2006).
Seeley, W. W., et al. "Neurodegenerative Diseases Target Large-Scale Human Brain Networks", Neuron, 62, pp. 42-52. (2009).
Sigurdsson, E. M. "Tau-Focused Immunotherapy for Alzheimer's Disease and Related Tauopathies", Curr Alzheimer Res., 6(5), pp. 446-450. (Oct. 2009).
Small, S. A., et al. "Linking Aβ and Tau in Late-Onset Alzheimer's Disease: A Dual Pathway Hypothesis", Neuron., 60(4), pp. 534-542. (2008).
Wu, T. T., et al. "An Analysis of the Sequences of the Variable Regions of Bence Jones Proteins and Myeloma Light Chains and Their Implications for Antibody Complementarity", J Exp Med,132, pp. 211-250. (1970).
Zhou, J., et al. "Predicting regional neurodegeneration from the healthy brain functional connectome", Neuron, 73(6), pp. 1216-1227. (2012).

* cited by examiner

BINDING MOLECULES THAT SPECIFICALLY BIND TO TAU

FIELD OF THE INVENTION

The invention relates to medicine. The invention in particular relates to binding molecules, e.g. antibodies or antigen-binding fragments thereof, that specifically bind to tau, and that are capable of inhibiting tau aggregation. The invention also relates to diagnostic, prophylactic and therapeutic methods using the anti-tau binding molecules.

BACKGROUND OF THE INVENTION

Dementia is a syndrome that can be caused by a number of progressive disorders that affect memory, thinking, behavior and the ability to perform everyday activities. About 36 million people worldwide are suffering from dementia today. The number of people with dementia is projected to double by 2030, and more than triple to 115.4 million people by 2050. Alzheimer's disease (AD) is the most common type of dementia. Currently, one in nine people age 65 and older (11 percent) and nearly half of those over age 85 have Alzheimer's disease. According to Alzheimer's Disease International, current global costs of caring for these patients exceeds $600 billion annually. These costs are likely to rise even faster than the prevalence of disease, especially in the developing world, as more formal social care systems emerge, and rising incomes lead to higher opportunity costs (Winblad, B and Jonsson, L, World Alzheimer Report 2010).

The brains of AD patients have an abundance of two abnormal structures, amyloid plaques and neurofibrillary tangles. This is especially true in certain regions of the brain that are important in memory. There is also a substantial loss of neurons and synapses in the cerebral cortex and certain subcortical regions. Both neurofibrillary tangles and neuronal loss increase in parallel with the duration and severity of illness (Gomez-Isla, t. et al, Ann Neurol 1997; 41:17-24) and neurofibrillary load has been shown to correlate with cognitive decline. (Braak, H. and Braak, E, Neurobiol Aging. 1997 July-August; 18(4):351-7.

Neurofibrillary tangles are intraneuronal lesions that are composed of hyperphosphorylated and insoluble accumulations of the microtubule-associated protein, tau. These accumulations are a histopathological feature of many neurodegenerative diseases, which are collectively known as tauopathies. Tauopathies include, e.g., Alzheimer's disease (AD), Pick's disease (PiD), progressive supranuclear palsy (PSP), corticobasal degeneration (CBD), and frontotemporal lobar degeneration (FTLD). In human tauopathies, pathology progresses from one brain region to another in disease-specific patterns (Braak, H. and Braak, E, Neurobiol Aging. 1997 July-August; 18(4):351-7, Raj et. al. Neuron 2012; 73:1204-1215, Seeley et. al. Neuron 2009; 62: 42-52. and Zhou et. al., Neuron 2012; 73:1216-1227), the underlying mechanism of which is not yet clear.

Tau pathology is involved in and may be a cause of many tauopathies. In its normal form, tau is a highly soluble microtubule-associated protein (Jeganathan et al., Biochemistry 2008; 47:10526-10539.) that binds and promotes the assembly of microtubules (Drechsel et al., Mol Biol Cell 1992; 3:1141-1154.). However, in tauopathies, tau becomes hyperphosphorylated, causing detachment from microtubules, and ultimately tau-tau aggregation and accumulation as neurofibrillary tangles that are visualized within dystrophic neurites and cell bodies (Mandelkow and Mandelkow, Cold Spring Harbor Perspect Med 2, 2012: a006247). The amount of tau pathology correlates with progressive neuronal dysfunction, synaptic loss, and functional decline in humans and transgenic mouse models (Arriagada et al., Neurology. 1992 March; 42(3 Pt 1):631-9, Bancher et al., Neurosci Lett 1993; 162:179-182., Polydoro et al., J. Neoroscience 2009; 29:10741-10749. and Small and Duff, Neuron. 2008 Nov. 26; 60(4):534-42). While there have been no tau mutations observed in Alzheimer's disease, mutations in the tau gene appear to cause some forms of frontotemporal dementia (Cairns et al, Am J Pathol, 2007; 171: 227-40), presenting with tau positive inclusions and signifying that tau dysfunction is sufficient to cause neurodegeneration. Moreover, pathological tau appears to be an integral part of Aβ-induced neurotoxicity in cell culture and transgenic animal models (Rapoport, M, PNAS, 2002; 99:9, 6364-6369., Roberson E D, et al, Science, 2007; 316:750-754, Nicholson A M, and Ferreira A, J Neurosci 2009; 29:4640-4651, Oakley H, J Neurosci 2006; 26(40):10129-10140.).

Passive and active immunizations against tau have been analyzed in mice using several different mouse models, including different phospho-tau peptides for active immunizations and anti-tau antibodies for passive immunotherapy (Asuni A A, et al, J Neurosci. 2007; 27(34):9115-9129., Sigurdsson E M. Curr Alzheimer Res. 2009; 6(5):446-450, Boutajangout A, et al, J Neurosci. 2010; 30(49):16559-16566., Rosenmann H, et al. Arch Neurol. 2006; 63(10): 1459-1467., Boimel M, et al, Exp Neurol. 2010; 224(2): 472-485.). Passive immunization with well-characterized anti-tau antibodies which react with phosphorylated Ser396 and Ser404 of the hyperphoshorylated tau protein at an early pathologic conformational epitope on tau, confirmed the results seen in active immunization studies. Mice treated with these antibodies showed marked reductions in tau pathology, which was measured by biochemical methods and histology, as well as a significant delay in loss of motor-function decline which was assessed in behavioral testings (Boutajangout A, et al, J Neurochem. 2011; 118(4): 658-667., Chai X, et al. J Biol Chem. 2011; 286(39):34457-34467.).

Currently the most prevalent medical approach for AD is to provide symptomatic therapy, which is not efficacious even after several years of treatment. New therapeutic approaches and strategies for AD need to go beyond the treatment of symptoms to prevent cognitive decline and counteract the fundamental pathological processes of the disease. In particular, there is a need for the development of molecules that either alone or in combination with other AD-targeted drugs interfere with at least some of the earliest stages of the disease. Such molecules would provide new, advantageous options in the early diagnosis (which could itself improve treatment outcomes), prevention, and treatment of AD and other tauopathies.

SUMMARY OF THE INVENTION

The present invention provides novel binding molecules, in particular human binding molecules, e.g. human antibodies or antigen-binding fragments thereof, capable of specifically binding to tau, and which are capable of inhibiting tau aggregation.

In a preferred embodiment, the binding molecules according to the present invention comprise a heavy chain CDR1 comprising the amino acid sequence of SEQ ID NO: 1, a heavy chain CDR2 comprising the amino acid sequence of SEQ ID NO: 2, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6.

In certain embodiments, the binding molecules are capable of inhibiting tau aggregation in vitro.

In certain embodiments, the binding molecules of the present invention comprise a heavy chain variable region comprising the amino acid sequence of SEQ ID NO: 7 and a light chain variable region comprising the amino acid sequence of SEQ ID NO: 8.

Preferably, the binding molecules according to the present invention are human monoclonal antibodies, or antigen-binding fragments thereof.

The invention also pertains to immunoconjugates, comprising at least one binding molecule according to the present invention and further comprising at least one tag.

Another aspect of the present invention relates to nucleic acid molecules encoding the binding molecules according to the present invention.

The binding molecules, immunoconjugates and/or nucleic acid molecules of the invention are suitable for use as a medicament, preferably for use in the diagnosis, prophylaxis and/or treatment of tauopathies, including but not limited to Alzheimer's disease (AD).

The invention also pertains to functional variants of the binding molecules according to the present invention.

The invention also pertains to pharmaceutical compositions comprising a binding molecule according to the present invention and/or an immunoconjugate, and a pharmaceutically acceptable carrier or excipient.

DEFINITIONS

Figure 1:
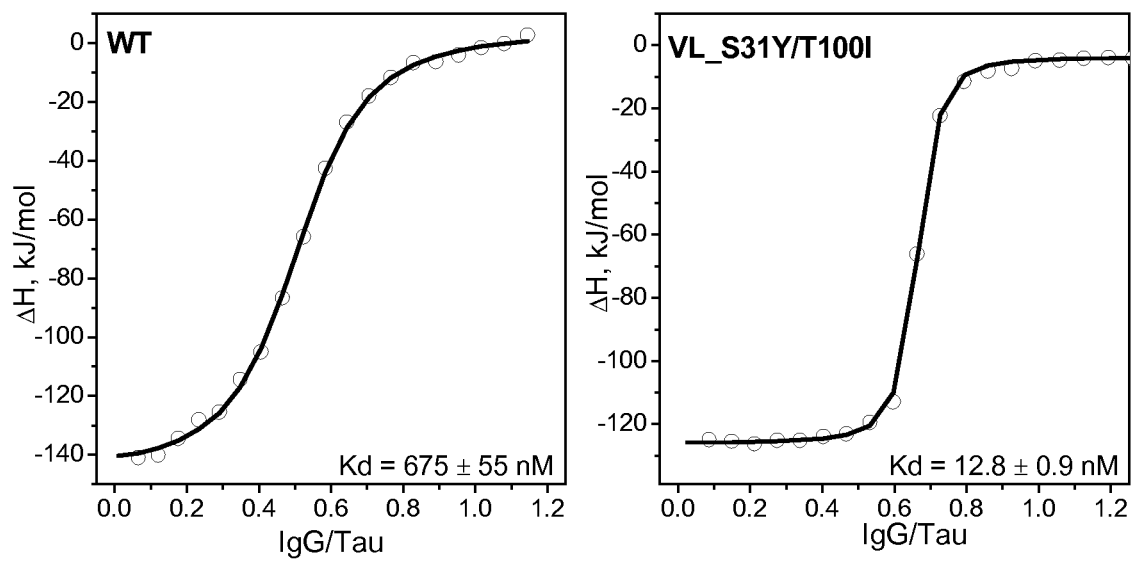
FIG. 1: Affinity measurements by Isothermal Titration Calorimetry.

As used throughout the present invention, the term "antigen-binding fragments" means a portion of an intact binding molecule, such as an antibody. Examples of antibody fragments include Fab, Fab', F(ab')2 and Fv fragments, CDR, antigen-binding site, heavy or light chain variable region, diabodies, triabodies single chain antibody molecules (scFv) and multispecific antibodies formed from at least two intact antibodies or fragments thereof or (poly) peptides that contain at least a fragment of an immunoglobin that is sufficient to confer antigen binding to the (poly) peptide, etc. An antigen-binding fragment may comprise a peptide or polypeptide comprising an amino acid sequence of at least 2, 5, 10, 15, 20, 25, 30, 35, 40, 50, 60, 70, 80, 90, 100, 125, 150, 175, 200, or 250 contiguous amino acid residues of the amino acid sequence of the antibody. The antigen-binding fragments may be produced synthetically or by enzymatic or chemical cleavage of intact immunoglobulins or they may be genetically engineered by recombinant DNA techniques. The methods of production are well known in the art and are described, for example, in Antibodies: A Laboratory Manual, edited by: E. Harlow and D, Lane (1988), Cold Spring Harbor Laboratory, Cold Spring Harbor, N.Y., which is incorporated herein by reference. An antibody or antigen-binding fragment thereof may have one or more binding sites. If there is more than one binding site, the binding sites may be identical to one another or they may be different.

An immunoglobulin light or heavy chain variable region consists of a "framework" region interrupted by "antigen-binding sites". The antigen-binding sites are defined using various terms as follows: (i) Complementarity Determining Regions (CDRs) are based on sequence variability (Wu and Kabat J Exp Med 132:211-50, 1970). Generally, the antigen binding site has three CDRs in each variable region (HCDR1, HCDR2 and HCDR3 in heavy chain variable region (VH) and LCDR1, LCDR2 and LCDR3 in light chain variable region (VL)) (Kabat et al., Sequences of Proteins of Immunological Interest, 5th Ed. Public Health Service, National Institutes of Health, Bethesda, Md., 1991). (ii) The term "hypervariable region", "HVR", or "HV" refers to the regions of an antibody variable domain which are hypervariable in structure as defined by Chothia and Lesk (Chothia and Lesk J Mol Biol 96:901-17, 1987). Generally, the antigen-binding site has three hypervariable regions in each VH (H1, H2, H3) and VL (L1, L2, L3). Chothia and Lesk refer to structurally conserved HVs as "canonical structures". Numbering systems as well as annotation of CDRs and HVs have recently been revised by Abhinandan and Martin (Abhinandan and Martin Mol Immunol 45:3832-9, 2008). (iii) Another definition of the regions that form the antigen-binding site has been proposed by Lefranc (Lefranc, et al. Dev Camp Immunol 27:55-77, 2003) based on the comparison of V domains from immunoglobulins and T-cell receptors. The International ImMunoGeneTics (IMGT) database (http://www imgt_org) provides a standardized numbering and definition of these regions. The correspondence between CDRs, HVs and IMGT delineations is described in Lefranc et al. The antigen-binding site can also be delineated based on Specificity Determining Residue Usage (SDRU) (Almagro J Mol Recognit 17:132-43, 2004), where Specificity Determining Residues (SDR), refers to amino acid residues of an immunoglobulin that are directly involved in antigen contact.

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply every antibody of the present invention. For example, depending on the position of the first CDR the following CDRs might be shifted in either direction.

"Framework" or "framework sequence" are the remaining sequences within the variable region of an antibody other than those defined to be antigen-binding site sequences. Because the exact definition of an antigen-binding site can be determined by various delineations as described above, the exact framework sequence depends on the definition of the antigen-binding site.

The term "monoclonal antibody" (mAb) as used herein means an antibody (or antibody fragment) obtained from a population of substantially homogeneous antibodies. Monoclonal antibodies are highly specific, typically being directed against a single antigenic determinant.

The term "specifically binding", or "specifically recognize", as used herein, in reference to the interaction of an antibody and its binding partner, e.g. an antigen, means that the interaction is dependent upon the presence of a particular amino acid sequence or structure, e.g. an antigenic determinant or epitope, on the binding partner. In other words, the antibody preferentially binds or recognizes the binding partner even when the binding partner is present in a mixture of other molecules or organisms. The binding may be mediated by covalent or noncovalent interactions or a combination of both. In yet other words, the term "specifically binding" or "specifically recognizes" means that the antibody is specifically immunoreactive with an antigenic determinant or epitope and is not immunoreactive with other antigenic determinants or epitopes. An antibody that (immuno)specifically binds to an antigen may bind to other peptides or polypeptides with lower affinity as determined by, e.g., radioimmunoassays (RIA), enzyme-linked immunosorbent assays (ELISA), BIACORE, or other assays known in the art. Antibodies or fragments thereof that specifically bind to an antigen may be cross-reactive with related antigens, carrying the same epitope. Preferably, antibodies or fragments thereof that specifically bind to an antigen do not cross-react with other antigens.

The term "epitope" as used herein means that part of the antigen that is contacted by the CDR loops of antibody. A "structural epitope" comprises about 15-22 contact residues on the the antigen surface and involves many amino acid residues that make contact with a large group of residues on CDRs collectively referred to as the paratope of antibody. Direct contact between epitope and paratope residues is established through electrostatic forces such as hydrogen bonds, salt bridges, van der Waals forces of hydrophobic surfaces and shape complementarity The interface has also bound water molecules or other co-factors that contribute to the specificity and affinity of antigen-antibody interactions The binding energy of an antigen-antibody complex is primarily mediated by a small subset of contact residues in the epitope-paratope interface. These "energetic residues" are often located in the center of the epitope-paratope interface and make up the functional epitope. Contact residues in the periphery of the interface make generally minor contributions to the binding energy; their replacements have frequently little effect on the binding with antigen. Thus, the binding or functional activity of an epitope involves a small subset of energetic residues centrally located in the structural epitope and contacted by the specificity-determining CDRs. The assignment of a functional epitope on an antigenic protein can be made using several methods including Alanine scan mutagenesis or by solving the crystal structure of the antigen with the antibody. An epitope can be linear in nature or can be a discontinuous epitope, e.g., a conformational epitope, which is formed by a spatial relationship between non-contiguous amino acids of an antigen rather than a linear series of amino acids. A conformational epitope includes epitopes resulting from folding of an antigen, where amino acids from differing portions of the linear sequence of the antigen come in close proximity in 3-dimensional space. For discontinuous epitopes, it may be possible to obtain binding of one or more linear peptides with decreased affinity to a so-called partial epitope, e. g. dispersed at different regions of the protein sequence (Cragg, M. S. (2011) Blood 118 (2): 219-20.).

As used herein, the term "affinity" refers to a measure of the strength of the binding of an individual epitope or partial epitope with the CDRs of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valences of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, N.Y. (1984), Kuby, Janis Immunology, W.H. Freeman and Company New York, N Y (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., KD, IC50, are preferably made with standardized solutions of antibody and antigen, and a standardized buffer.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid molecule" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

As used herein, the terms "treat" or "treatment" refer to both therapeutic treatment and prophylactic or preventative measures, wherein the object is to prevent or slow down (lessen) an undesired physiological change or disorder, such as the development of Parkinsonism or Alzheimer's Disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented. A "medicament" as used herein, is an agent used in the treatment of an undesirable physiological change or disorder.

By "subject" or "individual" or "animal" or "patient" or "mammal," is meant any subject, particularly a mammalian subject, e.g., a human patient, for whom diagnosis, prognosis, prevention, or therapy is desired.

DETAILED DESCRIPTION OF THE INVENTION

In a first aspect, the present invention provides binding molecules, e.g. antibodies and/or antigen-binding fragments thereof, that are capable of specifically binding to tau and that are capable of inhibiting tau aggregation, wherein the binding molecules comprises a heavy chain CDR1 comprising the amino acid sequence of SEQ ID NO: 1, a heavy chain CDR2 comprising the amino acid sequence of SEQ ID NO: 2, and a heavy chain CDR3 comprising the amino acid sequence of SEQ ID NO: 3, and a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6.

In a certain embodiment, the binding molecules of the present invention comprise a heavy chain variable region comprising the amino acid sequence of SEQ ID NO: 7 and a light chain variable region comprising the amino acid sequence of SEQ ID NO: 8.

According to the present invention, novel binding molecules are provided that specifically bind tau with very high affinity and that are capable of inhibiting the conversion of recombinant tau into PHF-like aggregates. In certain embodiments, the binding molecules are capable of inhibiting the in vitro conversion of recombinant tau into PHF-like aggregates.

In certain embodiments, the binding molecules specifically bind tau with an affinity of 20 nm or less, preferably 15 nm or less.

Tau is an abundant central and peripheral nervous system protein having multiple well-known isoforms. In the human central nervous system (CNS), six major tau isoforms ranging in size from 352 to 441 exist due to alternative splicing (Hanger, et al. Trends Mol Med 15:112-9, 2009). These isoforms differ from each other by the regulated inclusion of 0-2 N-terminal inserts, and 3 or 4 tandemly arranged microtubule-binding repeats, and are referred to as ON3R, 1N3R, 2N3R, ON4R, 1N4R and 2N4R. The recombinant tau as used herein refers to the tau isoform of SEQ ID NO: 9. The tau protein can be recombinantly expressed in high quantities, for example, in E. coli, baculovirus, mammalian or cell-free systems. Recombinant tau may be recombinantly expressed and purified using standard methods (e.g. Barghorn, et al 2005, Meth Mol Biol 35-51) or as described in Example 1.

In an embodiment, the binding molecules of the invention, such as antibodies or antigen-binding fragments thereof, specifically bind to a non-phosphorylated tau peptide of SEQ ID NO: 10 or SEQ ID NO: 11.

In certain embodiments, the binding molecule of the invention specifically bind to an epitope comprising the amino acid residues 299-318 of the tau protein.

In certain embodiments, the binding molecule of the invention specifically bind to an epitope comprising the amino acid residues 299-318 of the tau protein of SEQ ID NO: 9.

Tau binds microtubules and regulates transport of cargo through cells, a process that can be modulated by tau phosphorylation which occurs at many of the 79 potential serine (Ser) and threonine (Thr) phosphorylation sites. Tau is highly phosphorylated during brain development. The degree of phosphorylation declines in adulthood. Some of the phosphorylation sites are located within the microtubule binding domains of tau, and it has been shown that an increase of tau phosphorylation negatively regulates the binding of microtubules. For example, Ser262 and Ser396, which lie within or adjacent to microtubule binding motifs, are hyperphosphorylated in the tau proteins of the abnormal paired helical filaments (PHFs), a major component of the neurofibrillary tangles (NFTs) in the brain of AD patients. The term "paired helical filament-tau" or "PHF-tau" as used herein refers to well-known tau aggregates which make up the pathological structures called neurofibrillary tangles (NFT), first described by Alzheimer in the brain of dementia patient. Their presence is also found in numerous other diseases known as tauopathies. The term "neurofibrillary tangle" (NFT) refers to the pathological structures first described by Alzheimer in the brain of dementia patient. NFT are composed of orderly arranged subunits called paired helical filaments aggregates of hyperphosphorylated tau protein that are most commonly known as a primary marker of Alzheimer's Disease.

Physiological tau protein stabilizes microtubules in neurons. Pathological phosphorylation leads to abnormal tau localization and aggregation, which causes destabilization of microtubules and impaired cellular transport. Aggregated tau is neurotoxic in vitro (Khlistunova et al., J. Biol. Chem. 281 (2006), 1205-1214). The exact neurotoxic species remains unclear, however, as do the mechanism(s) by which they lead to neuronal death. Aggregates of tau can be observed as the main component of neurofibrillary tangles (NFT) in many tauopathies, such as Alzheimer's disease (AD), Frontotemporal dementias, supranuclear palsy, Pick's disease, Argyrophilic grain disease (AGD), corticobasal degeneration, FTDP-17, Parkinson's disease, Dementia pugilistica (Reviewed in Gendron and Petrucelli, Mol. Neurodegener. 4:13 (2009)). Besides these observations, evidence emerges that tau-mediated neuronal death can occur even in the absence of tangle formation. Soluble phospho-tau species are present in CSF (Aluise et al., Biochim. Biophys. Acta. 1782 (2008), 549-558). Tau aggregates can transmit a misfolded state from the outside to the inside of a cell and transfer between co-cultured cells (Frost et al., J. Biol. Chem. 284 (2009), 12845-12852).

According to the invention, novel binding molecules that specifically bind to tau and are capable of inhibiting the formation of tau aggregates. Thus, the binding molecules of the invention could serve as possible therapeutic reagents that prevent formation of tau pathology, as biomarkers to assess risks of developing AD or as reagents used to capture biomarkers that assess the risk of developing AD.

The binding molecules of the invention can be intact immunoglobulin molecules such as monoclonal antibodies, or the binding molecules can be antigen-binding fragments thereof, including, but not limited to, heavy and light chain variable regions, Fab, F(ab'), F(ab')2, Fv, dAb, Fd, complementarity determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to tau.

In a preferred embodiment the binding molecules of the invention are human monoclonal antibodies, and/or antigen-binding fragments thereof. The binding molecules may also be nanobodies, alphabodies, affibodies, FN3-domain scaffolds and other scaffolds based on domains in (human) repeat proteins, like Adnectins, Anticalins, Darpins, Centyrins, etc, or other scaffolds comprising epitope binding sequences.

The present invention also relates to pharmaceutical compositions comprising at least one binding molecule according to the invention, and at least a pharmaceutically acceptable excipient.

In yet a further aspect, the invention provides immunoconjugates, i.e. molecules comprising at least one binding molecule as defined herein and further comprising at least one tag. The tag(s) can be joined/conjugated directly to the human binding molecules through covalent bonding. Alternatively, the tag(s) can be joined/conjugated to the binding molecules by means of one or more linking compounds. Techniques for conjugating tags to binding molecules are well known to the skilled artisan. The tags of the immunoconjugates of the present invention may be therapeutic agents, but they can also be detectable moieties/agents. Tags suitable in therapy and/or prevention may be toxins or functional parts thereof, antibiotics, enzymes, other binding molecules that enhance phagocytosis or immune stimulation. Immunoconjugates comprising a detectable agent can be used diagnostically to, for example, assess if a subject is in the process of developing AD. Detectable moieties/agents include, but are not limited to, enzymes, prosthetic groups, fluorescent materials, luminescent materials, bioluminescent materials, radioactive materials, positron emitting metals, and non-radioactive paramagnetic metal ions. The tags used to label the binding molecules for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., phagocytosis assays), Western blotting applications, etc. Suitable labels for the detection/analysis/diagnosis techniques and/or methods known in the art are well within the reach of the skilled artisan.

It is another aspect of the present invention to provide nucleic acid molecules encoding at least a binding molecule, functional variant or immunoconjugate according to the invention. Such nucleic acid molecules can be used as intermediates for cloning purposes, e.g. in the process of affinity maturation as described above. In a preferred embodiment, the nucleic acid molecules are isolated or purified. The skilled man will appreciate that functional variants of these nucleic acid molecules are also intended to be a part of the present invention. Functional variants are nucleic acid sequences that can be directly translated, using the standard genetic code, to provide an amino acid sequence identical to that translated from the parental nucleic acid molecules.

It is another aspect of the invention to provide polynucleotides, e.g. vectors, comprising one or more nucleic acid molecules according to the present invention. Vectors can be derived from plasmids such as inter alia F, R1, RP1, Col, pBR322, TOL, Ti, etc; cosmids; phages such as lambda, lambdoid, M13, Mu, P1, P22, Qβ, T-even, T-odd, T2, T4, T7, etc; plant viruses. Vectors can be used for cloning and/or for expression of the binding molecules of the invention and might even be used for gene therapy purposes. Vectors comprising one or more nucleic acid molecules according to the invention operably linked to one or more expression-regulating nucleic acid molecules are also covered by the present invention. The choice of the vector is dependent on the recombinant procedures followed and the host used. Introduction of vectors in host cells can be effected by inter alia calcium phosphate transfection, virus infection, DEAE-dextran mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the invention as is well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr). Vectors comprising one or more nucleic acid molecules encoding the human binding molecules as described above operably linked to one or more nucleic acid molecules encoding proteins or peptides that can be used to isolate the human binding molecules are also covered by the invention. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional aspect of the present invention. Preferably, the hosts are host cells. Host cells include, but are not limited to, cells of mammalian, plant, insect, fungal or bacterial origin. Bacterial cells include, but are not limited to, cells from Gram-positive bacteria or Gram-negative bacteria such as several species of the genera *Escherichia*, such as *E. coli*, and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells, such as Chinese Hamster Ovary (CHO) cells, COS cells, BHK cells, NSO cells or Bowes melanoma cells are preferred in the present invention. Mammalian cells provide expressed proteins with posttranslational modifications that are most similar to natural molecules of mammalian origin. Since the present invention deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. In preferred embodiments, the human producer cells comprise at least a functional part of a nucleic acid sequence encoding an adenovirus E1 region in expressible format. In even more preferred embodiments, said host cells are derived from a human retina and immortalized with nucleic acids comprising adenoviral E1 sequences, such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6 is a registered trademark of Crucell Holland B.V.). For the purposes of this application "PER.C6 cells" refers to cells deposited under number 96022940 or ancestors, passages up-stream or downstream as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in WO 00/63403 the disclosure of which is incorporated herein by reference in its entirety.

A method of producing a binding molecule according to the invention is an additional aspect of the invention. In certain embodiments, the method comprises the steps of a) culturing a host according to the invention under conditions conducive to the expression of the binding molecule, and b) optionally, recovering the expressed binding molecule. The expressed binding molecules can be recovered from the cell free extract, but preferably they are recovered from the culture medium. The above method of producing can also be used to make functional variants of the binding molecules and/or immunoconjugates of the present invention. Methods to recover proteins, such as binding molecules, from cell free extracts or culture medium are well known to the man skilled in the art. Binding molecules, functional variants and/or immunoconjugates obtainable by the above-described method are also a part of the present invention.

Alternatively, next to the expression in hosts, such as host cells, the binding molecules and immunoconjugates of the invention can be produced synthetically by conventional peptide synthesizers or in cell-free translation systems using RNA nucleic acid derived from DNA molecules according to the invention. Binding molecules and immunoconjugates as obtainable by the above described synthetic production methods or cell-free translation systems are also a part of the present invention.

In yet a further aspect, the invention provides compositions comprising at least a binding molecule, preferably a human monoclonal antibody, according to the invention, at least a functional variant thereof, at least an immunoconjugate according to the invention and/or a combination thereof. In addition to that, the compositions may comprise, inter alia, stabilizing molecules, such as albumin or polyethylene glycol, or salts. Preferably, the salts used are salts that retain the desired biological activity of the binding molecules and do not impart any undesired toxicological effects. If necessary, the human binding molecules of the invention may be coated in or on a material to protect them from the action of acids or other natural or non-natural conditions that may inactivate the binding molecules.

In yet a further aspect, the invention provides compositions comprising at least a nucleic acid molecule as defined in the present invention. The compositions may comprise aqueous solutions such as aqueous solutions containing salts (e.g., NaCl or salts as described above), detergents (e.g., SDS) and/or other suitable components.

Furthermore, the present invention pertains to pharmaceutical compositions comprising at least a binding molecule, such as a human monoclonal antibody, of the invention (or functional fragment or variant thereof), at least an immunoconjugate according to the invention, at least a composition according to the invention, or combinations thereof. The pharmaceutical composition of the invention further comprises at least one pharmaceutically acceptable excipient or carrier. Pharmaceutically acceptable excipients and carriers are well known to the skilled person.

In certain embodiments, the pharmaceutical composition comprises at least one other prophylactic and/or therapeutic agent. Such agents can be binding molecules, small molecules, organic or inorganic compounds, enzymes, polynucleotide sequences, etc. These can be used in combination with the binding molecules of the invention. "In combination" herein means simultaneously, as separate formulations, or as one single combined formulation, or according to a sequential administration regimen as separate formulations, in any order.

In certain embodiments, the binding molecules are for use in inhibiting and/or prevention tau protein aggregation.

In certain embodiments, the binding molecules are for use as a medicament, and preferably for use in the diagnostic, therapeutic and/or prophylactic treatment of neurodegenerative diseases, such as AD. Thus, the binding molecules of the invention or fragments thereof can be used to treat, reduce or prevent symptoms in patients having a neurodegenerative disease that involves accumulation of tau or pathological tau or tau aggregation within the brain, such as patients suffering from AD as well as any other tauopathy or other tau-related pathologies in which tau may be overexpressed. While not wishing to be bound by any particular theory, the binding molecules of the invention may exert their beneficial effect by reducing or eliminating pathological tau or tau aggregation and hence the amount of PHF-tau in the brain. The binding molecules of the invention may be used to treat an animal patient belonging to any classification. Examples of such animals include mammals such as humans, rodents, dogs, cats and farm animals.

Another embodiment of the invention is a method for inhibiting and/or preventing tau protein aggregation.

Another embodiment of the invention is a method of treating or reducing symptoms of a neurodegenerative disease that involves aggregation of tau in a patient comprising administering to the patient a therapeutically effective amount of the binding molecule of the invention for a time sufficient to treat or reduce symptoms of the neurodegenerative disease. In any of the embodiments above, the neurodegenerative disease that involves aggregation of tau is a tauopathy. As used herein a "tauopathy" encompasses any neurodegenerative disease that involves the pathological aggregation of tau within the brain. In addition to familial and sporadic AD, other exemplary tauopathies are frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-StrausslerScheinker disease, Hallervorden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, nonguanamian motor neuron disease with neurofibrillary tangles, postencephalitic parkinsonism, and chronic traumatic encephalopathy, such as dementia pugulistica (boxing disease). (Morris, et al. Neuron 70:410-26, 2011).

A tauopathy-related behavioral phenotype includes cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

Patients amenable to treatment include asymptomatic individuals at risk of AD or other tauopathy, as well as patients presently showing symptoms. Patients amenable to treatment include individuals who have a known genetic risk of AD, such as a family history of AD or presence of genetic risk factors in the genome. Exemplary risk factors are mutations in the amyloid precursor protein (APP), especially at position 717 and positions 670 and 671 (Hardy and Swedish mutations, respectively). Other risk factors are mutations in the presenilin genes, PS 1 and PS2, and ApoE4, family history of hypercholesterolemia or atherosclerosis. Individuals presently suffering from AD can be recognized from characteristic dementia by the presence of risk factors described above. In addition, a number of diagnostic tests are available to identify individuals who have AD. These include measurement of cerebrospinal fluid tau and Aβ42 levels. Elevated tau and decreased AB42 levels signify the presence of AD. Individuals suffering from AD can also be diagnosed by AD and Related Disorders Association criteria.

Anti-tau binding molecules of the invention are suitable both as therapeutic and prophylactic agents for treating or preventing neurodegenerative diseases that involves accumulation of tau, and/or pathological aggregation of tau, such as AD or other tauopathies or tau-associated ailments. In asymptomatic patients, treatment can begin at any age (e.g., at about 10, 15, 20, 25, 30 years). Usually, however, it is not necessary to begin treatment until a patient reaches about 40, 50, 60, or 70 years. Treatment typically entails multiple dosages over a period of time. Treatment can be monitored by assaying antibody, or activated T-cell or B-cell responses to the therapeutic agent over time. If the response falls, a booster dosage is indicated.

In prophylactic applications, pharmaceutical compositions or medicaments are administered to a patient susceptible to, or otherwise at risk of, AD or other ailment involving tau, in an amount sufficient to eliminate or reduce the risk, lessen the severity, or delay the outset of the disease, including biochemical, histologic and/or behavioral symptoms of a disease, its complications and intermediate pathological phenotypes presented during development of the disease. In therapeutic applications, compositions or medicaments are administered to a patient suspected of, or already suffering from, such a disease in an amount sufficient to reduce, arrest, or delay any of the symptoms of the disease (biochemical, histologic and/or behavioral). Administration of a therapeutic may reduce or eliminate mild cognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, compositions or medicaments are usually administered in several dosages until a sufficient immune response has been achieved.

Anti-tau binding molecules or fragments thereof of the invention may be administered in combination with other agents that are effective for treatment of related neurodegenerative diseases. In the case of AD, antibodies of the invention may be administered in combination with agents that reduce or prevent the deposition of amyloid beta (Aβ). It is possible that PHF-tau and Aβ pathologies are synergistic. Therefore, combination therapy targeting the clearance of both PHF-tau and Aβ-related pathologies at the same time may be more effective than targeting each individually.

In the case of Parkinson's Disease and related neurodegenerative diseases, immune modulation to clear aggregated forms of the a-synuclein protein is also an emerging therapy. A combination therapy which targets the clearance of both tau and α-synuclein proteins simultaneously may be more effective than targeting either protein individually. In the methods of the invention, the "therapeutically effective amount" of the binding molecule, e.g. antibody or antigen-binding fragment thereof, in the treatment or ameliorating symptoms of a tauopathy can be determined by standard research techniques. For example, the dosage of the antibody can be determined by administering the agent to relevant animal models well known in the art.

In addition, in vitro assays can optionally be employed to help identify optimal dosage ranges. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems. The mode of administration for therapeutic use of the binding molecules of the invention may be any suitable route that delivers the agent to the host. Pharmaceutical compositions of these binding molecules are useful for parenteral administration, e.g., intradermal, intramuscular, intraperitoneal, intravenous, subcutaneous, intranasal or intracranial or they can be administered into the cerebrospinal fluid of the brain or spine.

The treatment may be given in a single dose schedule, or as a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease. Thus, a pharmaceutical composition of the invention for intramuscular injection could be prepared to contain 1 ml sterile buffered water, and between about 1 ng to about 100 mg, about 50 ng to about 30 mg or about 5 mg to about 25 mg of an antibody of the invention. Similarly, a pharmaceutical composition of the invention for intravenous infusion could be made up to contain about 250 ml of sterile Ringer's solution, and about 1 mg to about 30 mg or about 5 mg to about 25 mg of an antibody of the invention. Actual methods for preparing parenterally administrable compositions are well known and are described in more detail in, for example, "Remington's Pharmaceutical Science", 15th ed., Mack Publishing Company, Easton, Pa.

The binding molecules of the invention can be lyophilized for storage and reconstituted in asuitable carrier prior to use. This technique has been shown to be effective with antibodyand other protein preparations and art-known lyophilization and reconstitution techniques can be employed.

In certain embodiments, the binding molecules may be used in methods of diagnosing AD or other tauopathy in a subject. This method involves detecting, in the subject, the presence of tau using a diagnostic reagent such as an antibody or a fragment thereof of the present invention. Tau may be detected in a biological sample from a subject (e.g., blood, urine, cerebral spinal fluid) by contacting the biological sample with the diagnostic antibody reagent, and detecting binding of the diagnostic antibody reagent to PHF-tau in the sample from the subject. Assays for carrying out the detection include well known methods such as ELISA, immunohistochemistry, western blot, or in vivo imaging.

Diagnosis may be performed by comparing the number, size, and/or intensity of labeled tau, tau accumulation, tau aggregates, and/or neurofibrillary tangles in a sample from the subject or in the subject, to corresponding baseline values. The baseline values can represent the mean levels in a population of undiseased individuals. Baseline values can also represent previous levels determined in the same subject.

The diagnostic methods described above can also be used to monitor a subject's response to therapy by detecting the presence of tau in a subject before, during or after the treatment. A change in values relative to baseline signals a response to treatment. Values can also change temporarily in biological fluids as pathological tau is being cleared from the brain.

The present invention is further directed to a kit for performing the above described diagnostic and monitoring methods. Typically, such kits contain a diagnostic reagent such as the binding molecules of the invention, and optionally a detectable label. The diagnostic binding molecule, e.g. antibody, itself may contain the detectable label (e.g., fluorescent molecule, biotin, etc.) which is directly detectable or detectable via a secondary reaction (e.g., reaction with streptavidin). Alternatively, a second reagent containing the detectable label may be utilized, where the second reagent has binding specificity for the primary antibody. In a diagnostic kit suitable for measuring tau in a biological sample, the antibodies of the kit may be supplied pre-bound to a solid phase, such as to the wells of a microtiter dish.

The invention is further illustrated in the Examples, which are not intended to limit the invention in any way.

EXAMPLES

Example 1

Protein Expression and Purification huTau441 (SEQ ID NO: 9), the longest isoform of human Tau containing both N terminal inserts and all four microtubule binding motifs was expressed in *E. Coli* BL21 (DE3) bacterial strain as follows: A 10 L 2YT Broth culture was incubated at 37° C. to a density of OD600=1.0. IPTG was added to 1 mM and cultures were incubated for an additional 3 hrs. Bacterial cells were harvested by centrifugation and resuspended in PBS to wash away the remaining of the supernatant. After centrifugation, the pellets were stored at −80° C. until purification.

Pellets were resuspended in 5 ml/g pellet lysis buffer [Bugbuster mastermix, Merck-Millipore) plus Complete Ultra EDTA free protease inhibitors (Roche) and extra 500 U of Benzonase (Merck-Millipore). After 30 min at room temperature, the lysate was subjected to a 60 min heat treatment at 70° C. The precipitated material was removed by centrifugation and the soluble tau protein was isolated by affinity chromatography through a Ni Sepharose Excel (GE) column followed by C-Tag (Life Technologies) and gel filtrated through a Superdex 200 column on (Akta Avant 25, GE). An aliquot from each fraction containing protein was subjected to SDS-PAGE and fractions with the least amount of contaminating material (bands higher or lower than monomer tau) were kept for experimental purposes. In all cases, the preparation contained>95% monomer Tau protein as assessed by SEC-MALS.

Affinity Measurements

Affinities of the binding molecules of the present invention were determined using a Microcal Auto-iTC200 isothermal titration calorimeter (Malvern). Tau and tau antibodies were dialysed to PBS, pH 7.4 to ensure perfect buffer matching conditions. Tau protein (peptide) at 20 μM was incrementally titrated with CBTAU-27.1 stocks of 200 μM in PBS and the variations in enthalpy assessed after each injection. Data was fitted according to a one set of sites model using Microcal PEAQ-ITC Analysis Software (Malvern). Results are shown in FIG. 1.

Tau peptide encompassing residues 299-318 was titrated with the CBTAU27.1 (as described in WO2015/197820) (left panel) or the antibody of the present invention. The variations in enthalpy upon each injection are shown as a function of IgG/Tau molar ratio (○). The continuous lines represent the fit of the binding data to a "one set of binding sites" model. The equilibrium dissociation constants resulted from the fits are shown in the bottom right corners of each panel.

As can be seen the antibody of the present invention displays a much sharper binding curve than CBTAU-27.1 which quantitatively translates into a significant improvement in affinity. Thus, the dissociation constant characterizing the interaction of the antibodies with the peptide improved from 675 nm for CBTAU27.1 to 12.8 nm for the antibody of the present invention.

Figure 2:
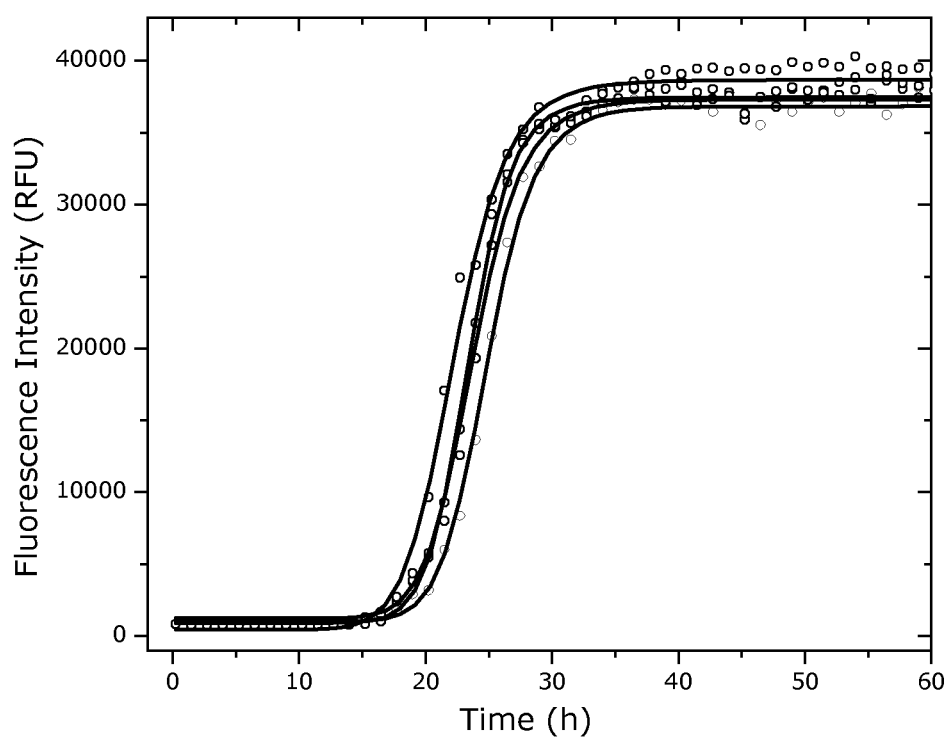
FIG. 2: In vitro Tau aggregation curves.

In Vitro Aggregation Assay huTau441 (15 μM) was incubated in PBS, pH 7.4 with heparin (8 μM) as conversion initiator and ThioflavinT (ThT) (50 μM) as fluorescence probe for the aggregation process. The aggregation was followed in continuous mode with orbital shaking (425 cpm, 3 mm) at 37° C. in a microplate format (Synergy Neo2, BioTek). The progress of Tau aggregation was assessed every 15 minutes by recording the ThT emission fluorescence at 485 nm (bandwidth of 20 nm) upon excitation at 440 nm (bandwidth of 20 nm). Results are shown in FIG. 2.

Four replicates of the conversion process are shown to highlight the high reproducibility of the assay. The spontaneous conversion of rTau showed to be very reproducible. The trend of the obtained kinetics was sigmoidal, with a well-defined lag phase followed by an exponential growth as it is expected for a nucleation dependent polymerization mechanism. In conclusion, this shows that a very reproducible assay was set up in which monomeric recombinant Tau is converted into ThT positive fibers. This assay was used to monitor the inhibitory effect of the CBTAU mAbs.

Atomic Force Microscopy

The converted protein samples were applied to a freshly cleaved mica substrate. After 2-3 min, the surface was extensively rinsed with ultrapure water to remove salts and unbound protein. The preparation was then dried in a stream of air and mounted on a microscope scanner. The images were recorded in tapping mode on a Digital Instruments Multimode atomic force microscope equipped with Nanoscope IV controller and a type E scanner (Bruker). All images were acquired using single beam silicon probes with a nominal spring constant of 40 N/m and nominal tip radius of 10 nm. The results are shown in FIG. 3.

Figure 3:
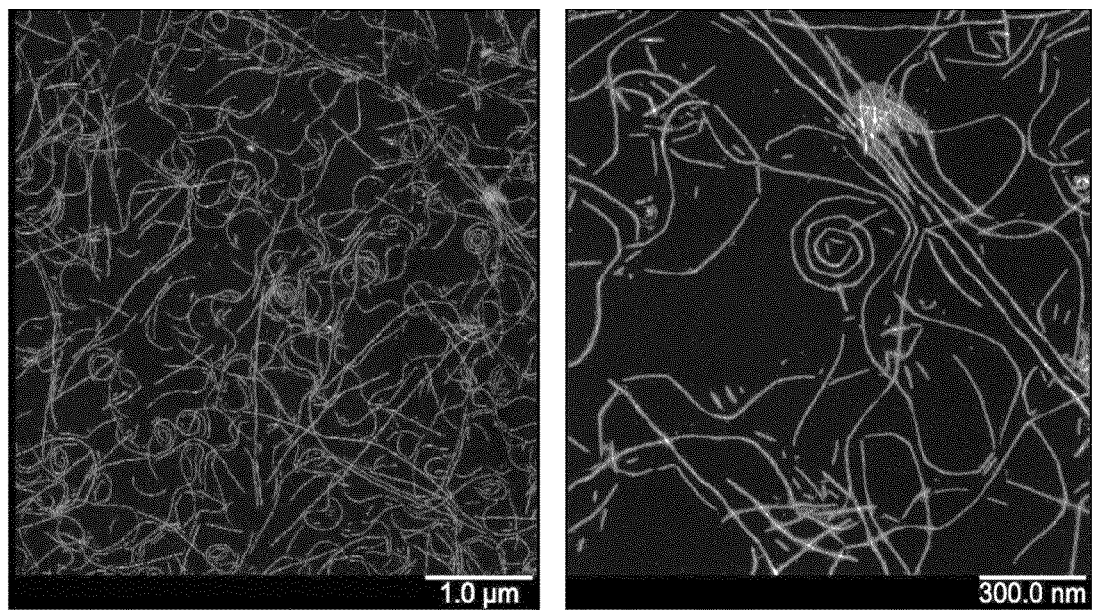
FIG. 3: AFM images of huTau441 fibrils.

FIG. 3 (A) shows a low magnification image illustrating the abundance and length variability of fibrils. FIG. 3(B) is a high-magnification image of individual fibrils highlighting their morphology. Fibrils were obtained upon incubation of the protein at 37° C. in PBS, pH 7.4.

As can be seen only fibrillar aggregates were observed, and the background of the sample looked very clean, without amorphous structures, showing there are no other parallel processes taking place. In the zoom image on the right, clear tangle structures are observed, thus indicating that the Tau fibers generated in our in vitro assay have similar morphologies withTau paired helical filaments isolated from AD brains.

Functionality of CBTAU mAbs huTau441 (15 μM) was incubated in PBS, pH 7.4 with heparin (8 μM) as conversion initiator and ThioflavinT (50 μM) as fluorescence probe for the aggregation process in the absence or presence of 3-9 μM CBTAU-27.1 variants. The aggregation was followed in continuous mode with orbital shaking (425 cpm, 3 mm) at 37° C. in a microplate format (Synergy Neo2, BioTek). The progress of Tau aggregation was assessed every 15 minutes by recording the ThT emission fluorescence at 485 nm (bandwidth of 20 nm) upon excitation at 440 nm (bandwidth of 20 nm).

Figure 4:
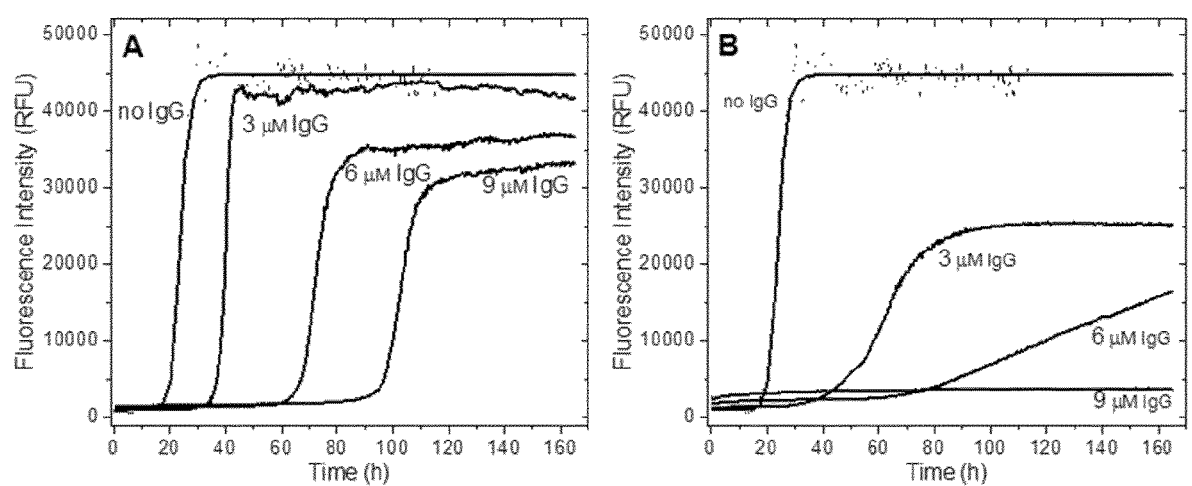
FIG. 4: Tau aggregation inhibition by control (A) and antibody of the invention (B) antibody.

In FIG. 4, the time course of huTau441 (15 mM) aggregation is shown in the absence and presence of IgGs as monitored by ThT fluorescence. The concentrations of IgGs corresponding to each experiment are shown next to the individual curves. The antibody according to the present invention (B) displays significant improvement efficiency in blocking Tau aggregation relative to CBTAU-27.1(A). While a dose dependent partial inhibition is observed for CBTAU-27.1 reflected by increases in lag time and lower final ThT values, the inhibitory effects seen for the antibody of the present invention are much more dramatic with total tau aggregation inhibition observed at 9 μM antibody concentration. Conversion of huTau441 was not affected by the presence of negative control antibodies (data not shown).

These results indicate that affinity of CBTAU-27.1 to Tau is directly correlated with its efficiency to block Tau aggregation and that the 50-fold improvement in affinity for the antibody of the present invention has proven to have a dramatic increase on the ability of the antibody to block the Tau aggregation process.

Sequences:

|  | CDR1 (SEQ ID NO:) | CDR2 (SEQ ID NO:) | CDR3 (SEQ ID NO:) |
|---|---|---|---|
| HC | DYWTA (1) | IIYSGDSDTRYHPSVQG (2) | LDARVDAGWQLDS (3) |
| LC | KSSQSVFYRDNNKNYLA (4) | WASSRES (5) | QHYFNIPHN (6) |

Heavy Chain Variable Region (SEQ ID NO 7):
QVQLVESGPEMRKPGESLKISCKTSGYIFS DYWTAWVRQLPGKGLQWMGIIYSGDSDTR YHPSVQGHVTMSTDSSLTTAYLQWSSLKASDTGIYY CARLDARVDAGWQLDSWGQGT LVTVSS Light Chain Variable Region (SEQ ID NO 8):
DIQLTQSPDSLAVSLGERATINC KSSQSVFYRDNNKNYLAWYQHKSGQPPKLLFF WASSRESGVSDRFSGSGSGTDFTLTIDNLQAEDVALY YCQHYFNIPHNFGQGTKLEIK SEQ ID NO 9:
MAEPRQEFEVMEDHAGTYGLGDRKDQG-GYTMHQDQEGDTDAGLKESPLQTPTEDGSE EPG-SETSDAKSTPTAEDVTAPLVDEGAPGKQAAAQPH-TEIPEGTTAEEAGIGDTPSLEDE AAGHVTQARMVSKSKDGTGSDDKKAKGADGKTKI-ATPRGAAPPGQKGQANATRIPAK TPPAPKTPPSSGEPPKSGDRSGYSSPGSPGTPGSRSRTP SLPTPPTREPKKVAVVRTPPKSP SSAKSRLQTAPVPMPDLKNVKSKIG-STENLKHQPGGGKVQIINKKLDLSNVQSKCGSKD NIKHVPGGGSVQIVYKPVDL-SKVTSKCGSLGNIHHKPGGGQVEVKSEKLDFKDRVQ SKI GSLDNITHVPGGGNKKI-ETHKLTFRENAKAKTDHGAEIVYKSPVVSGDT-SPRHLSNVSST GSIDMVDSPQLAT-LADEVSASLAKQGL

SEQ ID NO 10:
299HVPGGGSVQIVYKPVDLSKV

SEQ ID NO 11:
299HVPGGGSVQIVYKPVDL-SKVTSKCGSLGNIHHKPGGGQVEVKSEKLDFKDRVQ SKIG SLDNITHVPGGGNK

The invention claimed is:

1. A binding molecule that is adapted to specifically bind to tau, comprising:
   a heavy chain CDR1 comprising the amino acid sequence of SEQ ID NO: 1,
   a heavy chain CDR2 comprising the amino acid sequence of SEQ ID NO: 2,
   a heavy chain CDR3 comprising the amino acid sequence of SEQ ID NO: 3,
   a light chain CDR1 comprising the amino acid sequence of SEQ ID NO: 4,
   a light chain CDR2 comprising the amino acid sequence of SEQ ID NO: 5, and
   a light chain CDR3 comprising the amino acid sequence of SEQ ID NO: 6,
   wherein the binding molecule is capable of inhibiting aggregation of tau.

2. A binding molecule according to claim 1, wherein the binding molecule comprises a heavy chain variable region comprising the amino acid sequence of SEQ ID NO: 7 and a light chain variable region comprising the amino acid sequence of SEQ ID NO: 8.

3. A binding molecule according to claim 1, wherein the binding molecule is a human monoclonal antibody, or an antigen-binding fragment thereof.

4. A binding molecule according to claim 2, wherein the binding molecule is a human monoclonal antibody, or an antigen-binding fragment thereof.

5. A method of inhibiting aggregation of tau protein, comprising exposing the tau protein to a binding molecule according to claim 1.

6. A method of inhibiting aggregation of tau protein, comprising exposing the tau protein to a binding molecule according to claim 2.

7. A method for the diagnosis, prophylaxis or treatment of a neurodegenerative disease that involves accumulation of tau, and/or pathological aggregation of tau in a patient, comprising administering a binding molecule according to claim 1 to the patient.

8. A method of diagnosis, prophylaxis or treatment of a neurodegenerative disease that involves accumulation of tau, and/or pathological aggregation of tau in a patient, comprising administering a binding molecule according to claim 2 to the patient.

9. The method according to claim 7, wherein the neurodegenerative disease is Alzheimer's disease.

10. The method according to claim 8, wherein the neurodegenerative disease is Alzheimer's disease.

11. A nucleic acid molecule encoding a binding molecule according to claim 1.

12. A nucleic acid molecule encoding a binding molecule according to claim 2.

13. A vector, comprising a nucleic acid molecule according to claim 11.

14. A vector, comprising a nucleic acid molecule according to claim 12.

15. A pharmaceutical composition, comprising:
    a binding molecule according to claim 1, and
    a pharmaceutically acceptable carrier or excipient.

16. A pharmaceutical composition, comprising:
    a binding molecule according to claim 2, and
    a pharmaceutically acceptable carrier or excipient.

17. An immunoconjugate, comprising:
    at least one binding molecule according to claim 1, and
    at least one tag.

18. An immunoconjugate, comprising:
    at least one binding molecule according to claim 2, and
    at least one tag.

19. A pharmaceutical composition comprising:
    an immunoconjugate according to claim 17, and
    a pharmaceutically acceptable carrier or excipient.

20. A pharmaceutical composition, comprising:
    an immunoconjugate according to claim 18, and
    a pharmaceutically acceptable carrier or excipient.

\* \* \* \* \*

SEQUENCE LISTING

<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: HC CDR1

<400> SEQUENCE: 1

Asp Tyr Trp Thr Ala
1               5

<210> SEQ ID NO 2
<211> LENGTH: 17
<212> TYPE: PRT
<213> ORGANISM: Artificial Sequence
<220> FEATURE:
<223> OTHER INFORMATION: HC CDR2

<400> SEQUENCE: 2

Ile Ile Tyr Ser Gly Asp Ser Asp Thr Arg Tyr His Pro Ser Val Gln
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: HC CDR3

<400> SEQUENCE: 3

Leu Asp Ala Arg Val Asp Ala Gly Trp Gln Leu Asp Ser
1               5                   10

<210> SEQ ID NO 4
<211> LENGTH: 17
<212> TYPE: PRT
<213> ORGANISM: Artificial Sequence
<220> FEATURE:
<223> OTHER INFORMATION: LC CDR1

<400> SEQUENCE: 4

Lys Ser Ser Gln Ser Val Phe Tyr Arg Asp Asn Asn Lys Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: LC CDR2

<400> SEQUENCE: 5

Trp Ala Ser Ser Arg Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LC CDR3

-continued

```
<400> SEQUENCE: 6

Gln His Tyr Phe Asn Ile Pro His Asn
1               5

<210> SEQ ID NO 7
<211> LENGTH: 122
<212> TYPE: PRT
<213> ORGANISM: Artificial Sequence
<220> FEATURE:
<223> OTHER INFORMATION: HC variable region

<400> SEQUENCE: 7

Gln Val Gln Leu Val Glu Ser Gly Pro Glu Met Arg Lys Pro Gly Glu
1               5                   10                  15

Ser Leu Lys Ile Ser Cys Lys Thr Ser Gly Tyr Ile Phe Ser Asp Tyr
            20                  25                  30

Trp Thr Ala Trp Val Arg Gln Leu Pro Gly Lys Gly Leu Gln Trp Met
        35                  40                  45

Gly Ile Ile Tyr Ser Gly Asp Ser Asp Thr Arg Tyr His Pro Ser Val
    50                  55                  60

Gln Gly His Val Thr Met Ser Thr Asp Ser Ser Leu Thr Thr Ala Tyr
65                  70                  75                  80

Leu Gln Trp Ser Ser Leu Lys Ala Ser Asp Thr Gly Ile Tyr Tyr Cys
                85                  90                  95

Ala Arg Leu Asp Ala Arg Val Asp Ala Gly Trp Gln Leu Asp Ser Trp
            100                 105                 110

Gly Gln Gly Thr Leu Val Thr Val Ser Ser
        115                 120

<210> SEQ ID NO 8
<211> LENGTH: 113
<212> TYPE: PRT
<213> ORGANISM: Artificial Sequence
<220> FEATURE:
<223> OTHER INFORMATION: LC Variable region

<400> SEQUENCE: 8

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Arg
            20                  25                  30

Asp Asn Asn Lys Asn Tyr Leu Ala Trp Tyr Gln His Lys Ser Gly Gln
        35                  40                  45

Pro Pro Lys Leu Leu Phe Phe Trp Ala Ser Ser Arg Glu Ser Gly Val
    50                  55                  60

Ser Asp Arg Phe Ser Gly Ser Gly Ser Gly Thr Asp Phe Thr Leu Thr
65                  70                  75                  80

Ile Asp Asn Leu Gln Ala Glu Asp Val Ala Leu Tyr Tyr Cys Gln His
                85                  90                  95

Tyr Phe Asn Ile Pro His Asn Phe Gly Gln Gly Thr Lys Leu Glu Ile
            100                 105                 110

Lys

<210> SEQ ID NO 9
<211> LENGTH: 441
<212> TYPE: PRT
<213> ORGANISM: Artificial Sequence
<220> FEATURE:
<223> OTHER INFORMATION: Recombinant tau protein
```

<400> SEQUENCE: 9

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
```

```
                    405                 410                 415
Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 10
<211> LENGTH: 20
<212> TYPE: PRT
<213> ORGANISM: Artificial Sequence
<220> FEATURE:
<223> OTHER INFORMATION: non-phosphorylated tau peptide

<400> SEQUENCE: 10

His Val Pro Gly Gly Gly Ser Val Gln Ile Val Tyr Lys Pro Val Asp
1               5                   10                  15

Leu Ser Lys Val
            20

<210> SEQ ID NO 11
<211> LENGTH: 71
<212> TYPE: PRT
<213> ORGANISM: Artificial Sequence
<220> FEATURE:
<223> OTHER INFORMATION: non-phosphorylated tau peptide

<400> SEQUENCE: 11

His Val Pro Gly Gly Gly Ser Val Gln Ile Val Tyr Lys Pro Val Asp
1               5                   10                  15

Leu Ser Lys Val Thr Ser Lys Cys Gly Ser Leu Gly Asn Ile His His
            20                  25                  30

Lys Pro Gly Gly Gly Gln Val Glu Val Lys Ser Glu Lys Leu Asp Phe
        35                  40                  45

Lys Asp Arg Val Gln Ser Lys Ile Gly Ser Leu Asp Asn Ile Thr His
    50                  55                  60

Val Pro Gly Gly Gly Asn Lys
65                  70
```